United States Patent [19]

Neri et al.

[11] Patent Number: 4,895,715

[45] Date of Patent: Jan. 23, 1990

[54] METHOD OF TREATING GYNECOMASTIA

[75] Inventors: Rudolph Neri, Hawthorne; Robert J. Spiegel, Westfield, both of N.J.

[73] Assignee: Schering Corporation, Kenilworth, N.J.

[21] Appl. No.: 351,261

[22] Filed: May 9, 1989

Related U.S. Application Data

[63] Continuation of Ser. No. 181,286, Apr. 14, 1988, abandoned.

[51] Int. Cl.$^4$ .............. A61K 31/56; A61K 45/06; A61K 31/135; A61K 31/16
[52] U.S. Cl. ............................ 424/10; 514/171; 514/613; 514/651; 514/922
[58] Field of Search ............ 424/10, 171; 514/178, 514/613, 651, 922

[56] References Cited

U.S. PATENT DOCUMENTS

| | | | |
|---|---|---|---|
| 3,875,229 | 4/1975 | Gold | 260/562 R |
| 3,995,060 | 11/1976 | Neri et al. | 424/324 |
| 4,094,994 | 6/1978 | Schonenberger et al. | 424/341 |
| 4,097,578 | 6/1978 | Perronnet et al. | 424/273 |
| 4,239,776 | 12/1980 | Glen et al. | 424/304 |
| 4,310,523 | 1/1982 | Newmann | 424/240 |
| 4,329,364 | 5/1982 | Neri et al. | 424/324 |
| 4,386,080 | 5/1983 | Crowley et al. | 424/209 |
| 4,472,382 | 9/1984 | Labrie et al. | 424/177 |
| 4,536,516 | 8/1985 | Harper et al. | 514/514 |
| 4,598,072 | 7/1986 | Schwelkert et al. | 514/170 |
| 4,636,505 | 1/1987 | Tucker | 514/256 |
| 4,659,516 | 4/1987 | Bowler et al. | 260/397.5 |
| 4,659,695 | 4/1987 | Labrie | 514/15 |

FOREIGN PATENT DOCUMENTS

| | | |
|---|---|---|
| 637389 | 3/1964 | Belgium . |
| 078158 | 5/1983 | European Pat. Off. . |

OTHER PUBLICATIONS

Neri, R. and Monahan, M., *Invest. Urology* (1972) 10, pp. 123–130.

Nieschlay, E. and Loriaux, D. L., *Z. Klin Chem Klin Biochem* (1972), 4, p. 164.

Boyorski, S. et al. Trans. of Amer. Assoc. of Genito-Urinary Surgeons, (1977), 68, pp. 29–32.

Marsh, D. A. et al., J. Med. Chem. 1985, vol. 28, pp. 788–795.

*Primary Examiner*—Douglas W. Robinson
*Assistant Examiner*—Raymond J. Henley, III
*Attorney, Agent, or Firm*—Thomas D. Hoffman; Gerald S. Rosen; Eric S. Dicken

[57] ABSTRACT

A method of treating gynecomastia in noncastrated patients being treated with an antiandrogen for androgen-dependent diseases such as benign prostatic hypertrophy, who are in need of such treating comprising administering to such patients therapeutically effective amounts of an antiandrogen, e.g., flutamide, in association with an antiestrogen, e.g., Tamoxifen, or an aromatase inhibitor such as 4-hydroxyadrostenedione is disclosed.

10 Claims, No Drawings

METHOD OF TREATING GYNECOMASTIA

This is a continuation, of application Ser. No. 181,286 filed 4/14/88 now abandoned.

BACKGROUND

This invention relates to a method of treating gynecomastia in patients being treated with an antiandrogen who are in need of such treatment. This invention more particularly relates to a method of treating gynecomastia in benign prostatic hypertrophy patients being treated with an antiandrogen who are in need of such treating comprising administering to such patients in assocation with therapeutically effective amounts of an antiandrogen, an antiestrogen or an aromatase inhibitor or pharmaceutical compositions thereof.

U.S. Pat. No. 4,472,382, (Labrie et al.) discloses that prostate adenocarcinoma, benign prostate hypertrophy and hormone-dependent mammary tumors may be treated with various LH-RH agonists and that prostate adenocarcinoma and benign hypertrophy may be treated by use of various LH-RH agonists and an antiandrogen. However, there is no suggestion or disclosure of the present invention.

U.S. Pat. No. 4,659,695 (Labrie) discloses a method of treatment of prostate cancer in susceptible male animals including humans whose testicular hormonal secretions are blocked by surgical or chemical means, e.g., by use of an LH-RH agonist, e.g., [D-Trp$^6$, des-Gly-NH$_2$$^{10}$]LH-RH ethylamide which comprises administering an antiandrogen, e.g., flutamide in association at least one antiandrogen, e.g., flutamide in association at least one inhibitor of sex steroid biosynthesis, e.g., aminoglutethimide and/or ketoconazole. However, there is no suggestion or disclosure of the present invention.

U.S. Pat. 3,995,060 (Neri et al.) discloses methods of preparing certain antiandrogens including 4'-substituted and 3',4'-disubstituted anilides, e.g. flutamide, and their use in treating androgen-dependent or androgen-caused disease states, such as prostatic adenocarcinoma benign prostate hypertrophy, hirsutism, and acne, in mammals, including man. However, there is no suggestion or disclosure of this invention.

Benign prostatic hypertrophy, a particularly common problem in older men, has been treated with antiandrogens and by use of estrogenic substances. The use of estrogenic substances has undesirable, life-threatening side effects due to the inherent properties of the estrogenic substances.

The use of antiandrogens while devoid of life-threatening side effects associated with treatment with estrogenic substances produces gynecomastia in 50 to 60% of non-castrated males studied, including normal subjects and advanced prostate cancer patients. Gynecomastia interferes with continued patient compliance with the antiandrogen therapy.

There is a need for a method of treating gynecomastia in patients being treated with an antiandrogen who are in need of such treatment.

SUMMARY OF THE INVENTION

The invention provides a method of treating gynecomastia in patients being treated with an antiandrogen in need of such treating which comprises administering to such patients a therapeutically effective amount of an antiestrogen or an aromatase inhibitor or a pharmaceutical composition thereof.

In another aspect, the present invention provides a method of treating gynecomastria in benign prostatic hypertrophy patients in need of such treating which comprises admnistering to such patients in association with therapeutically effective amounts of an antiandrogen in association with an antiestrogen or an aromatase inhibitor or pharmaceutical compositions thereof.

DETAILED DESCRIPTION OF THE INVENTION

In one preferred aspect, the present invention provides an effective method of treating gynecomastia in patients being treated with an antiandrogen to treat androgen-dependent or androgen-caused disease states, for example, benign prostate hypertrophy, which patients are in need of such treating by administering therapeutically effective amounts of the antiandrogen in association with an antiestrogen or an aromatase inhibitor or pharmaceutical compositions thereof. The active compounds may be administered together or in any order, as discussed hereinafter.

By the term "patients in need of such treating" is meant "male patients with functioning gonads who are being treated with antiandrogen and who exhibit or are likely to exhibit symptoms of gynecomastia". Male patients with functioning gonads have not been surgically castrated or chemically castrated by chronic administration of a LH-RH agonist or antagonist.

The administration of an antiandrogen, e.g. flutamide, to such non-surgically or non-chemically castrated male patients results in an increase in testosterone levels and levels of leutinizing hormone (LH). Testosterone is enzymatically aromatized into estrogens which estrogens are believed to produce breast enlargement and tenderness i.e., gynecomastia, observed in about 50–60% of patients being treated with a pure antiandrogen such as flutamide. In addition, the increasing levels of LH also stimulate testicular interstitial cells to produce not only testosterone but also estrogen. This increased release of estrogen is thought to result in gynecomastia. By administering an antiestrogen or an aromatase inhibitor to non-chemically or non-surgically castrated patients being treated with an antiandrogen for an androgen-dependent disease, e.g., benign prostate hypertrophy, such patients will continue to receive the beneficial effect of the antiandrogen in the hyperplastic (enlarged) prostate without the gynecomastia observed in patients treated with the antiandrogen alone.

To assist in determining the effect of the treatment, blood plasma concentration of testosterone (T), dihydrotestosterone (DHT), the estrogen 17$\beta$-estradiol (E$_2$), leuterining hormone (LH) and prostate acid phosphatase (AP) as well as prostate volume, urinary flow rate, hesitancy and nocturia are measured. Lowered concentrations of the male and female sex steroids, LH and prostatic AP, a reduction in prostate volume, hesitancy and nocturia as well as an increase in urinary flow rate are indicative of successful treatment of gynecomastia and BPH. The concentrations of the above listed components in plasma are measured by standard methods well known to those skilled in the art; see, for example, R. Neri and M. Monahan, Invest. Urology (1972), 10, 123–130 for prostatic AP staining and E. Nieschlay and D.L. Loriaux, Z. Klin Chem. Klin Biochem (1972), 4, 164 for radioimmunoassay determinations of T.

The prostate volume is measure by rectal examination and/or by transrectal ultrasonography. Objective assessment of the effect of treatment is also measured by physical methods well known to these skilled in the art of nuclear magnetic resonance imaging, as well as by physical examination. The response guidelines for investigation of benign prostate hypertrophy developed by S. Boyorski et al. Trans. of Amer. Assoc. of Genito-Urinary Surgeons, (1977), 68, 29–32 may also be used.

The use of therapeutically effective amounts of the antiestrogen or of the aromatase inhibitor in association with the antiandrogen in accordance with this invention effectively treats and usually totally prevents gynecomastia.

Typical suitable antiandrogens include nonsteroidal antiandrogens such as the imidazolidines, especially 1-(3'-trifluoromethyl-4'-nitrophenyl)-4,4-dimethylimidazoline-2,5-dione (also called Anandron) described in U.S. Pat. No. 4,097,578, or 4'-nitro-3-trifluoromethylisobutyranilide (also called flutamide) described in U.S. Pat. No. 429,364, hydroxyflutamide described in U.S. Pat. No. 3,875,229 and prodrug forms of hydroxyflutamide as well as the N-(phenylalkanoyl)aniline derivatives disclosed in U.S. Pat. No. 4,386,080 and the 3,4-disubstituted—branched—chain acylanilides disclosed in U.S. Pat. No. 4,239,776 (A. T. Glen et al.) and U.S. Pat. No. 4,636,505 (H. Tucker).

Typical suitable steroidal antiandrogens include 6-chloro-1,2-dihydro-17-(acetyl)-3'H-cyclopropa[1,2]-pregna-1,4,6-triene-3,20-dione, available under the tradename of Androcur from Schering A. G., W. Berlin.

The use of pure antiandrogens such as flutamide is preferred. By the term "pure antiandrogen" is meant an antiandrogen which is devoid of any androgenic, estrogenic, antiestrogenic, progestational, antiprogestational, angunadotrophic or adrenocortical activity.

Typical suitable antiestrogens include those steroidal and non-steroidal antiestrogens such as (1RS,2RS)-4,4'-diacetoxy-5,5'-difluoro-(1-ethyl-2-methylene)-di-m-phenylenediacetate, which is available from Biorex under the tradename of Acefluranol, 6α-chloro-16α-methylpregn-4-ene-3,20-dione which is available from Eli Lilly & Co., Indianaopolis, Ind. under the tradename of Clometherone, 6-chloro-17-hydroxypregna-1,4,6-triene3,20-dione which is available as the acetate salt from Syntex Labs, Palo Alto, Calif. as Delmadione Acetate, 17-hydroxy-6-methyl-19-norregna-4,6-diene-3,20-dione which is available from Theramex under the name of Lutenyl, 1-[2-[4-[1-(4-methoxyphenyl)-2-nitro-2-phenylethenyl]phenoxy]ethyl]-pyrrolidine which is available as the citrate salt from Parke-Davis Div. of Warner-Lambert Co., Morris Plains, N.J. under the name of Nitromifene Citrate, substituted aminoalkoxyphenylalkenes such as (Z)-2-[4-(1,2-diphenyl-1-butenyl)phenoxy]-N,N-dimethylethanamine which is available as the citrate salt from Stuart Pharmaceuticals, Wilmington, Del. as Tamoxifin Citrate (see also Belgian Pat. No. 637,389, Mar. 1964 and U.S. Pat. No. 4,536,516), 3,4-dihydro-2-(p-methoxyphenyl)-1-naphthyl-p-[2-(1-pyrrolidinyl)ethoxy]-phenyl ketone which is available as the methane sulfonate salt from Eli Lilly & Co. under the tradename of Trioxifene Mesylate, 1-[4'-(2-dimethylaminoethoxy)-phenyl]-1-(3'-hydroxyphenyl)-2-phenyl-but-1-ene, which is available from Klinge Pharma, 6-hydroxy-2-(p-hydroxyphenyl)-benzo(b)thien-3-yl[2-(1-pyrrolidinyl)-ethoxyphenyl]keyone which is available from Eli Lilly & Co. (LY-117018), [6-hydroxy-2-(4-hydroxyphenyl)benzo(b)-thien-3yl]-[4-(2-(1-piperdinyl)-ethoxy)phenyl]methanone, which is available from Eli Lilly & Co. as the hydrogen chloride salt (LY-1567-58) and meso-3,4-bis(3'-hydroxyphenyl) hexane as well as the dimethyl, dipropyl and 3'-acetoxyphenyl analogues which are described in U.S. Pat. No. 4,094,994 and a series of 1-phenyl-alkane and -alkenes, e.g. (E)-3-cyclopentyl-1-(4-hydroxyphenyl)-1-phenyl-1-butene and 2-cyclopentyl-1-[4-hydroxy- or methoxyphenyl]-3-phenyl-2-propen-1-ol, FC-1157 which is available as the citrate salt from Farmos Group Ltd., Turku, Finland (see also Eur. Pat. Appln. No. EP 78,158 and ICI 164384 and other 7α-alkylamide derivatives of 17β-estradiol disclosed in U.S. Pat. No. 4,659,516 (J. Bowler et al). The preferred antiestrogens include Tamoxifen, FC-1157 and ICI 164384. Pure antiestrogens, i.e. compounds like ICI 164384 entirely free of estrogenic activity are more preferred.

By the term "aromatase inhibitor" is meant a substance that inhibits the aromatic conversion of tesosterone into estradiol.

Typical suitable aromatase inhibitors include 4-hydroxyandrosta-4,6-diene-3,17-dione (hereinafter "4-hydroxyandrostadienedione" as well as other 4-hydroxyandrostenedione derivatives and their non-bulky esters, e.g. 4-acetoxyandrostenedione which are disclosed by D. A. Marsh et al. in J. Med. Chem., 1985, Vol. 28, pp 788–795, aminoglutethimide available from Ciba Pharmaceuticals Co., Summit, N.J. under the tradename Cytadren and ketoconazole, available from Janssen Pharmaceutical, Piscataway, N.J. under the tradename Nizoral. The use of a pure aromatase inhibitor such as, 4-hydroxyandrostadienedione is preferred. Aminoglutethimide and ketoconazole are effective aromatase inhibitors but also inhibit adrenal sex steroid biosynthesis. Thus, when aminoglutethmide or ketoconazole is administered in accordance with the present invention, cortisol biosynthesis is blocked. Accordingly, hydrocortisone is administered in physiological amounts sufficient to maintain normal glycocorticoid levels when ketoconazole or aminoglutethimide is administered in association with an antiandrogen in accordance with the present invention.

In this invention, the antiandrogen, and the antiestrogen or aromatase inhibitor are administered as pharmaceutical compositions via parenteral or oral means. Preferably the antiandrogen, the antiestrogen or the aromatase inhibitor and hydrocortisone (when used) are administered orally.

The amount of each component administered is determined by the attending clinicians taking into consideration the etiology and severity of the disease, the patient's condition and age, the potency of each component and other factors.

The antiandrogen compositions are generally administered in a dosage range of about 0.20 to 40 mg/kg (body weight) per day with 250 to 750 mg per day in three equally divided doses being preferred.

The antiestrogen compositions (when used) are administered in a dosage range of about 0.1 to 10 mg/kg body weight per day, with 10 mg to 25 mg/day in two equally divided doses being preferred.

The aromatase inhibitor compositions (when used) are generally administered in a dosage range of about 25–250 mg/daily.

The aminoglutethimide compositions (when used) are administered initially in a dosage of about 250 mg given at 8-hour intervals and the dosage may be increased in increments of about 250 mg daily up to a total daily dose of about 2 grams.

The hydrocortisone compositions (when used) are administered orally in a dosage range of about 0.1 to 20 mg/kg body weight per day. Preferably, the hydrocortisone is administered orally at a dose of about 10 mg in the morning and about 5 mg doses in the afternoon and in the evening.

The ketoconazole compositions (when used) are administered orally in a dose of about 250 mg given at 8-hour intervals and may be increased to about 2 grams per day.

In a preferred aspect of this invention, the antiandrogen is 4'-nitro-3'-trifluoromethylisobutyranilide, i.e. flutamide, which is administered orally in a daily dose of about 250 mg; the aromatase inhibitor is 4-hydroxyandrostendione, which is administered orally in a daily dose of about 250 mg. In another preferred aspect of this invention, when the aromatase inhibitor is aminoglutethimide or ketoconazole, each is administered orally in three equally divided doses of 250 mg every 8 hours. Additionally, when aminoglutethimide or ketoconazole is administered, hydrocortisone is administered orally at a dose of about 10 mg in the morning and about 5 mg doses in the afternoon and in the evening.

The antiandrogen, the antiestrogen and the aromatase inhibitors may be compounded into a dosage form suitable for oral or parenteral administration. A tablet or capsule or caplets are particularly convenient forms for oral administration. Such compositions useful in the present invention are typically formulated with conventional pharmaceutical excipients, e.g., spray dried lactose and magnesium stearate into tablets or capsules for oral administration. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycols. Of course, taste improving substances can be added in the case of oral administration forms.

As further forms of administration, one can use plug capsules, e.g. hard gelatin, as well as closed softgelatin capsules comprising a softner or plasticizer, e.g. glycerine. The plug capsules contain the active substance preferably in the form of a granulate, e.g., in mixtures with fillers, such as lactose, saccharose, mannitol, starches such as potato starch or amylopectin, cellulose derivatives or highly-dispersed silicic acids. In softgelatin capsules, the active substance is preferably dissolved or suspended in suitable liquids, such as vegetable oils or liquid polyethylene glycols.

The active ingredient components used in accordance with the present invention may also be formulated into once-a-day or even longer sustained release composition by conventional techniques well known in the art.

In place of oral administration, the active compounds may be administered parenterally. In such case, one can use a solution of the active substance, e.g., in sesame oil or olive oil.

Following the above treatment using the described regimen, gynecomastia is inhibited, in some cases completely prevented, when treating androgen-dependent diseases such as benign prostatic hypertrophy in accordance with this invention.

What is claimed is:

1. A method of treating gynecomastia in patients being treating with a non-steroidal antiandrogen who are in need of such treating which comprises admnistering to such patients a therapeutically effective amount of an antiestrogen or 4-hydroxyandrostenedione.

2. A method according to claim 1 wherein 4-hydroxyandrostenedione is administered.

3. A method of treating gynecomastia in benign prostatic hypertrophy patients in need of such treating which comprises admnistering to such patients therapeutically effective amounts of a non-steroidal antiandrogen in association with an antiestrogen or 4-hydroxyandrostenedione.

4. A method according to claim 3 wherein a steroidal antiestrogen is administered.

5. A method according to claim 3, wherein a non-steroidal antiestrogen is administered.

6. A method according to claim 3 wherein the non-steroidal antiandrogen is 4'-nitro-3'-trifluoromethylisobutyranilide.

7. A method of treating gynecomastia in benign prostate hypertrophy patients in need of such treating which comprises administering to such patients therapeutically effective amounts of a non-steroidal antiandrogen in association with an antiestrogen.

8. A method of claim 7, wherein the non-steroidal antiandrogen is 4'-nitro-3-trifluoromethylisobutyranilide.

9. A method of claim 7 wherein the antiestrogen is a non-steroidal antiestrogen.

10. A method of claim 7 wherein the antiestrogen is a steroidal antiestrogen.

* * * * *